United States Patent [19]

Upshaw et al.

[11] 4,081,866
[45] Apr. 4, 1978

[54] TOTAL ANATOMICAL KNEE PROSTHESIS

[75] Inventors: Jackson E. Upshaw, Corpus Christi, Tex.; Charles Edward Meisch, Jersey City, N.J.

[73] Assignee: Howmedica, Inc., New York, N.Y.

[21] Appl. No.: 764,844

[22] Filed: Feb. 2, 1977

[51] Int. Cl.² .............................................. A61F 1/24
[52] U.S. Cl. .................................. 3/1.911; 128/92 C
[58] Field of Search ........................ 3/1.911, 1.91, 1.9, 3/1; 128/92 C, 92 CA

[56] References Cited

U.S. PATENT DOCUMENTS

| | | | |
|---|---|---|---|
| 3,728,742 | 4/1973 | Averill et al. | 3/1.911 |
| 3,774,244 | 11/1973 | Walker | 3/1.911 |
| 3,798,679 | 3/1974 | Ewald | 3/1.911 |
| 3,816,855 | 6/1974 | Saleh | 3/1.911 |
| 3,869,731 | 3/1975 | Waugh et al. | 3/1.911 |
| 3,924,277 | 12/1975 | Freeman et al. | 3/1.911 |
| 3,964,106 | 6/1976 | Hutter, Jr. et al. | 3/1.911 |

FOREIGN PATENT DOCUMENTS 1,390,494   4/1975   United Kingdom .................. 3/1.911

OTHER PUBLICATIONS

The Spherocentric Knee, by Matthews et al., Clinical Orthopaedics, No. 94, July-Aug. 1973, pp. 234-240.
Howmedica Knee System Bicompartmental With Cruciate Retention (Trade Brochure), 1975, showing Townley Total Knee Prosthesis.
Howmedica Knee System Bicompartmental Without Cruciate Retention (Trade Brochure), 1975, showing Total Condylar Knee Prosthesis.

Primary Examiner—Ronald L. Frinks
Attorney, Agent, or Firm—Pennie & Edmonds

[57] ABSTRACT

A prosthetic knee joint comprising cooperating femoral and tibial components that allow controlled rotational movement during extension and flexion, simulating the anatomical movement characteristics of the natural knee joint.

9 Claims, 10 Drawing Figures

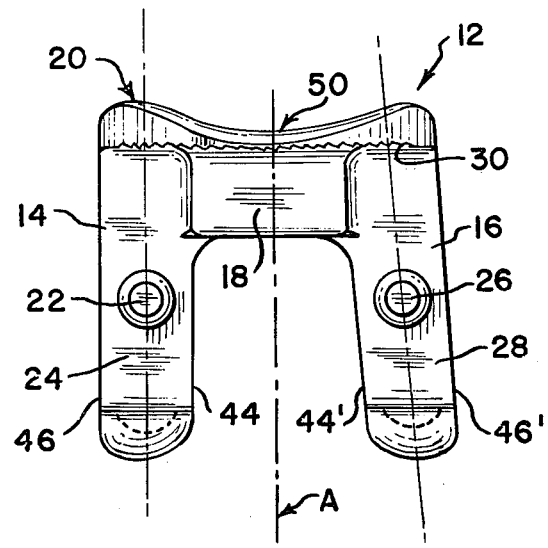
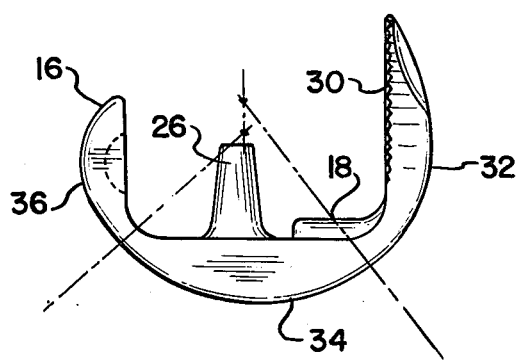
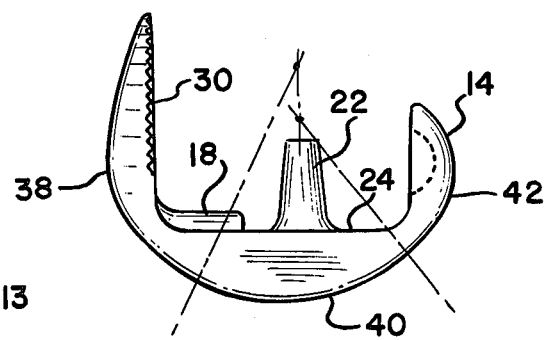
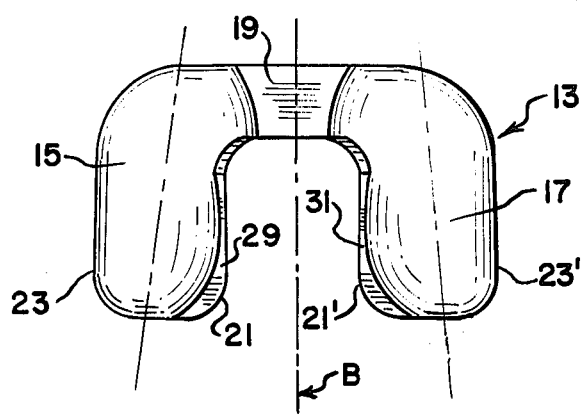
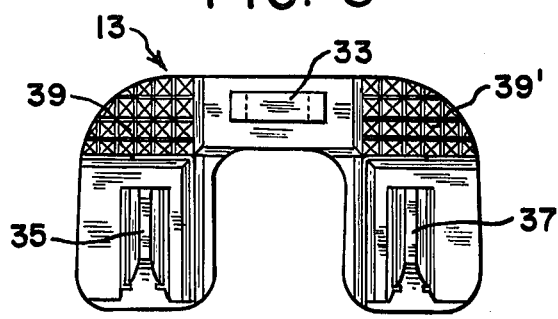
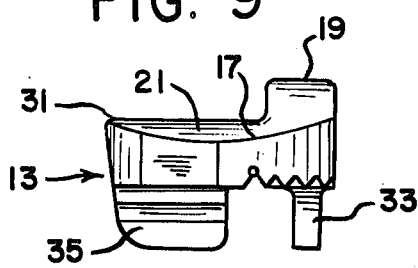
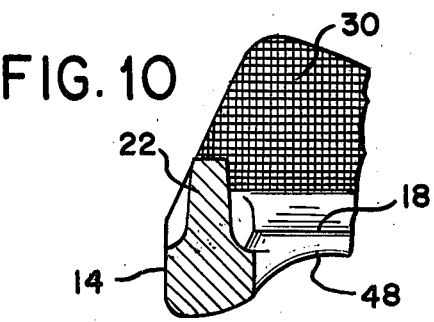

TOTAL ANATOMICAL KNEE PROSTHESIS

BACKGROUND OF THE INVENTION

This invention is concerned with a prosthetic replacement device and more particularly a total knee joint, providing simulation of the normal movement characteristics of the articulating surfaces of the natural knee joint, in particular rotation and derotation during flexion and extension. While the knee joint is usually considered to be a hinge joint, which implies that its movements are flexion and extension about a horizontal axis, the large size and incongruent shapes of the articulating condylar surfaces of the femur are such that the normal movement of the knee also allows for controlled rotation and the translatory movement of the knee joint actually occurs about three spatial axes.

A large number of various forms of knee arthroplasty have been proposed in recent years in an attempt to provide the equivalent of these general patterns of movement and articular geometry. Generally, there are two major types of knee prostheses: hinged and non-hinged. In one form, the knee is resected and replaced by a metal hinged-type device with deep penetration of the intermedullary canal in both the femur and the tibia by means of flared and thick distal fixation stems. Such devices have been previously decribed by Shiers, Young, and Walldius. While these devices provide stability during flexion-extension of the knee, they only permit motion about a single axis and do not allow for abduction-adduction rotation during flexion and extension. The range of movement is limited and patients are seldom able to flex the knee beyond 90°. Moreover, implantation requires the removal of a significant amount of the bone with a shortening of the limb if for any reason the prosthesis must be removed for subsequent arthrodesis.

More recent prostheses using a different approach attempt to structurally resurface both of the articulating surfaces of the knee to provide a non-hinged type prosthesis. Such devices have been previously described as unicondylar, such as the POLYCENTRIC prosthesis, or dual condylar, such as the GEOMEDIC prosthesis. Each, however, relies upon identical femoral condylar articulating surfaces with identical longitudinal and transverse cross-sections. Such condylar articulating features are different from the normal knee and they do not allow for the same movement found in the normal knee, providing only a partial duplication of the natural knee movement.

Still others create a mold of the distal femoral condyles providing circumduction in different planes and requiring the use of a long intermedullary canal stem and severance of both the collateral and cruciate ligaments. Such devices have been described by Ewald, Helfet, Aufranc and Turner. Even with the use of methylmethacrylate for cement fixation, these devices have unstable characteristics since the complexity of the knee movement tends to cause considerable torsional stress and eventual wear and weakening of the joint.

SUMMARY OF THE INVENTION

The object of this invention is to provide an improved knee prosthesis that will provide for a greater range of anatomical motion about the three spatial axes that control movement in the normal knee while allowing for retention of the collateral ligaments and the cruciate ligaments that lie within the fibrous capsule of the knee joint. This objective is attained by the present invention by creating an improved weight bearing prosthesis wherein the femoral and tibial components cooperate to provide a mutual but restricted articulatory engagement. The femoral component is of the dual condylar type with a uniquely contoured configuration wherein the individual condylar support members have the same transverse cross-sectional profile but with different configurations in the longitudinal direction, providing articulation on a tibial component with concave superior converging surfaces.

The prosthetic knee joint comprises cooperating femoral and tibial component, said femoral component having bone fixation means for implantation in the human femur and a pair of spaced condylar support members joined by an intercondylar segment. The condylar support members comprise a medial member and a lateral member with the longitudinal axis of said medial member being disposed at an anteriorly convergent angle of from about 3 to 7 degrees with respect to the longitudinal axis of said femoral component.

Each of said condylar support members has a downwardly facing convex articulating surface with interior and exterior sides whose profile in transverse cross-section is defined by a circular arc extending upwardly to the interior sides of said articulating surface and whose longitudinal cross-sectional configuration is defined by a condylar curve having at least three radii of curvature. Each said curve comprises a central section and a pair of terminal sections and the radius of curvature of the posterior terminal section of each said curve is smaller than the radii of curvature of the central and anterior terminal sections of said curve. The condylar curve of said lateral member has at least one central portion radius of curvature larger than the central portion radii of said medial member.

The tibial component has bone fixation means for implantation in the human tibia and has a pair of spaced plateau members joined by an intercondylar eminence segment. The plateau members comprise a medial and lateral bearing surface, each with interior and exterior sides, wherein the longitudinal axis of the medial and lateral bearing members are both canted, being disposed at an anteriorly convergent angle of from about 3 to 7 degrees with respect to the longitudinal axis of said tibial component. The angle of convergence of each of said bearing members is substantially equal to the angle of convergence of said medial condylar support member. Each of said bearing members has an upwardly facing concave articulating surface for cooperating with the corresponding convex articulating surface of said condylar support member defined by a circular arc whose radius of curvature is at least as large as the largest radius of curvature of said corresponding condylar support member.

The plateau bearing surfaces each have in transverse cross-section a profile defined by a portion of a circular quadrant smoothly merging to a portion that is substantially horizontally tangent to said quadrant, said quadrant portion curving upwardly to the interior side of said bearing surface to form side walls for guiding the articulating movement of the condylar support members. This unique configuration has been found to provide sufficient rotation-derotation during flexion and extension to approximate anatomic motion. As the prosthesis approaches its allowed limit of movement, it is checked or further limited by guide wall surfaces that rise above the bearing surfaces of the tibial plateau and form a continuous circumflexed wall on the interior and posterior sides of said bearing surfaces. Better weight distribution has also been found by providing concaved bearing surfaces that are as wide or preferably wider than the corresponding femoral condylar members. To provide for added stability, the present invention also employs a non-symmetrical patellar articulating surface that, together with an intercondylar support base, connects the medial and lateral support members to each other.

DETAILED DESCRIPTION OF THE DRAWINGS

The present invention will be better understood by reference to the accompanying drawings that illustrate a practical embodiment of a total knee prosthesis, wherein:

FIG. 4 is a superior elevational view of the femoral component shown in FIG. 3.

FIGS. 5 and 6 are views of the medial and lateral condylar curvilinear profiles, respectively;

FIG. 7 is a superior elevational view of the tibial component shown in FIG. 3;

FIG. 8 is an inferior elevational view of the tibial component shown in FIG. 7;

FIG. 9 is a lateral elevational view of the tibial component of FIG. 7; and

FIG. 10 is a partial posterior plan view of the lateral side of the femoral component.

Figure 1:
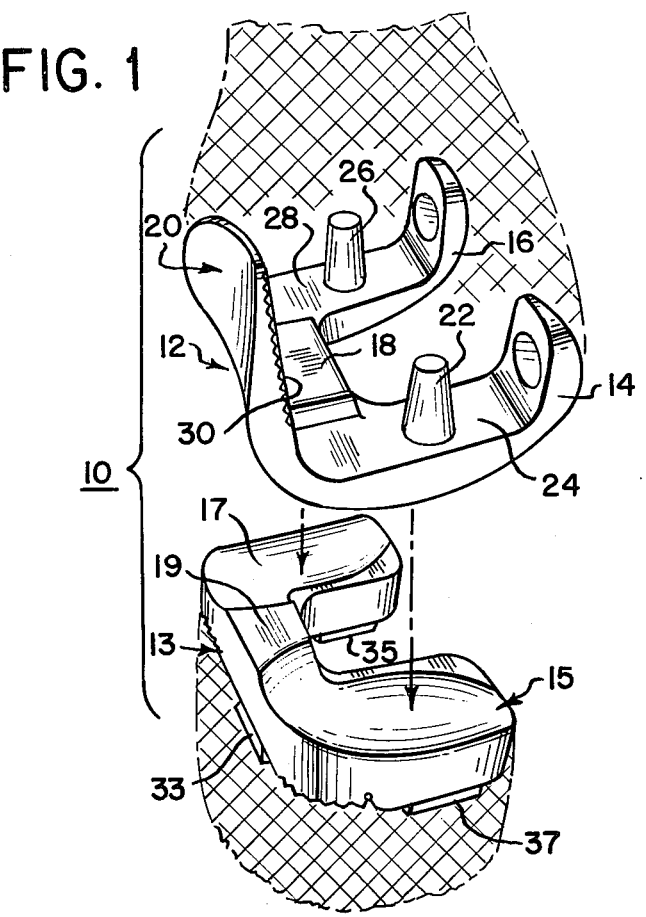
FIG. 1 is a diagramatic perspective view of a total knee prosthesis as it would appear in the human knee after implantation.
Figure 2:
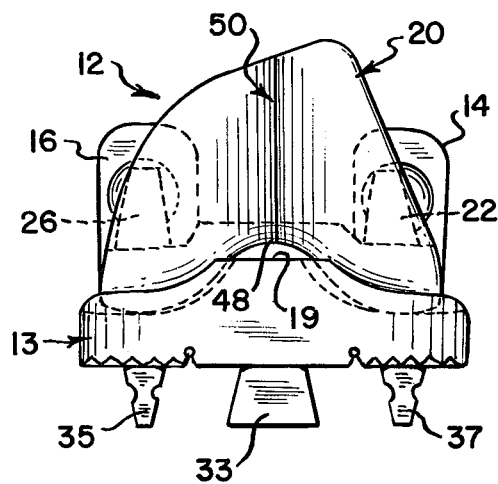
FIG. 2 is an anterior plan view of the prosthesis shown in FIG. 1.

Referring more particularly to FIG. 1 of the drawings, after surgical exposure of the knee joint and suitably preparing and osteotomizing the surfaces of the femur and tibia, reference number 10 shows generally a total knee prosthesis implanted in the left leg comprising a dual condylar femoral component shown at 12 and a tibial component shown at 13. Various ligaments and tendons which interconnect the bones and regulate and determine the articulating motion of the knee joint have not been shown but the general outline of the lower end of the femur and the upper end of the tibia have been illustrated. Reference numerals 14 and 16 designate, respectively, a pair of spaced femoral condylar support members with the lateral condylar member shown at 14 and the medial condylar member shown at 16. The condylar support members are connected by an intercondylar segment or support base 18 and a non-symmetrical patellar articulating surface flange 20 that helps to insure stability and maintain correct alignment of the condyles even if drifting in the bone occurs after long-term use. The shape of each said articulating surface is in longitudinal cross-section defined by a condylar curve. The condylar curves of the lateral condylar support member 14 and the medial condylar support member 16 are non-identical as is fully described in reference to FIGS. 5 and 6.

The femoral component also includes stud 22 extending upwardly from inner surface 24 of the lateral condylar support member 14 and a stud 26 extending upwardly from inner surface 28 of the medial condylar support member 16 for anchoring the femoral component to the femur. Such anchoring means are conveniently received in a resected area of the femur. To improve the anchoring of the femoral component of the femur, the inferior side of the patellar articulating surface 20 is provided with a serrated face 30 so that is has a waffled appearance which, after receiving surgical cement, facilitates securing the femoral component 12 to the femur, providing more positive cement fixation. With this arrangement, the fixation studs 22 and 26 can be relatively short as compared to the conventional intermedullar stems or fixation fins used in other dual condylar prostheses.

In accordance with the present invention, condylar curves of the femoral condylar members 14 and 16 are uniquely formed in that each curve is generated from different radii of curvature. As shown in FIGS. 5 and 6, the condylar curve of each condylar member has at least three sections. The condylar curve of medial condylar support member 16 is divided into an anterior terminal section 32, a central section 34, and a posterior terminal section 36. Likewise, condylar curve of lateral condylar support member 14 is divided into an anterior terminal section 38, a central section 40 and a posterior terminal section 42. Each section may possess one or more radii, the same radii preferably being used to generate the terminal sections 32 and 38 of condylar members 14 and 16. Likewise, terminal sections 36 and 42 preferably employ identical radii. However, the radii of curvature of posterior terminal sections 36 and 42 of condylar members 14 and 16 are smaller than the radii of curvature of the central and anterior terminal sections. As shown in FIG. 6, the radius of curvature of the central section 40 of the condylar curve of lateral condylar member 14 or average radius of curvature is larger than the radius of curvature or average radius of curvature of the central section 34 of the condylar curve of medial condylar member 16. The differing dimensions of the lateral and medial condylar curves resulting from the use of a radius of curvature in the lateral condylar curve larger than the radius of curvature 34 of the medial condylar curve as described above promote the desired rotational motion during flexion and extension.

While the curvilinear surfaces of condylar support members 14 and 16 are different in longitudinal cross-section, the transverse cross-sectional profile of the two articulating surfaces can be identical. As shown in FIG. 4, each condylar member has an interior side 44 and 44' and an exterior side 46 and 46' and the transverse cross-sectional profile for each condylar support member 14 and 16 is defined by a portion of a circular arc that extends primarily in an upward and inward direction on the interior side 44 of each condylar member in the area that lies next to the cruciate ligaments over a substantial portion of said transverse cross-section.

When condylar support members 14 and 16 are joined anteriorly through a patellar articulating surface member 20, an interior intercondylar notch 48 is formed by the confluence of the upwardly curved transverse cross-sectional portions of the condyles. This notch allows for controlled interaction with intercondylar eminence notch 19 of the tibial component 13 to allow adequate articulation while preventing anterior displacement with knee motion and minimizing a floating or shifting femoral component.

The patellar articulating flange 20 adds stability to the prosthesis while providing a concaved bearing surface 50 for receiving the natural patella or a replacement patella prosthesis. In some embodiments a non-symmetrical flange may be desired.

It has been found that the controlled rotation movement desired for simulating the anatomical movement characteristics of the natural knee joint can be further promoted by canting one of the condylar members. As shown in FIG. 4, the medial condylar member 16 is disposed at an anteriorly convergent angle of from about 3 to 7 degrees with respect to the longitudinal axis A of the femoral component 12, while the lateral condylar member 14 is preferably substantially parallel to longitudinal axis A.

In accordance with the present invention, tibial component 13 has a superior articulating plateau surface comprising two concave condylar bearing members 15 and 17 as shown in FIGS. 1 and 7. As shown in FIG. 9, each of the concave surfaces of these bearing members has a shape whose longitudinal cross-section is defined by a circular arc whose radius is larger than or equal to the largest radius of curvature of the corresponding condylar support member.

The plateau bearing members 15 and 17 are connected anteriorly by an intercondylar eminence member 19 that rises substantially above the circumduction plane of the plateau bearing members 15 and 17. As shown in FIGS. 7 and 8, the intercondylar eminence member 19 only joins the bearing members at the anterior part of the tibia, thus creating an opening in the posterior intercondylar area to allow for retention of the cruciate ligaments. Each of the plateau bearing members 15 and 17 is disposed at an anteriorly convergent angle of from about 3 to 7 degrees with respect to the longitudinal axis B of the tibial component 13. The angle of convergence of both the medial and lateral plateau bearing members is substantially equal to the angle of convergence of the medial condylar support member 16. The transverse cross-sectional profile of the plateau bearing members 15 and 17 is defined by a portion of a circular quadrant 25 that smoothly merges into a portion 27 that is substantially horizontally tangent to said quadrant. The radius of curvature for said circular quadrant is substantially equal to the corresponding radius of curvature of said condylar support members 14 and 16 in their transverse cross-section. The circular quadrant curves upwardly at the interior sides 21 and 21' from each bearing surface to form interior condylar guide side walls 29 and 31. The guide side walls 29 and 31 extend around and along a portion of the posterior end of each plateau bearing surface. These guide walls, together with the uniquely contoured femoral component, have been found to be particularly effective in providing the controlled movement necessary in a prosthesis when simulating the anatomical movement of the natural knee.

Figure 3:
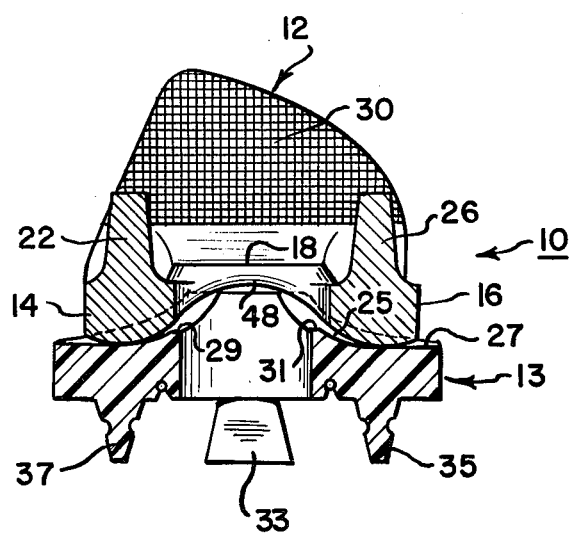
FIG. 3 is a posterior cross-sectional view of the prosthesis shown in FIG. 1.

For implanting the tibial component 13 in the tibia, this invention employs a downwardly directed bone fixation fin 33 underneath the intercondylar eminence member 19 for anchoring the tibial component anteriorly in the tibia. In addition, the tibial component as shown in FIGS. 3 and 8 has a pair of spaced fixation fins 35 and 37 depending from the underside of each bearing surface member 15 and 17 for further anchoring the tibial component, usually in a resected area of the tibia. As in the case of the patellar articulating surface 20, the anterior portion of the lower surface of the concaved bearing surface is provided with serrations 39 and 39' which permit the tibial component 13 to be firmly anchored by the use of suitable cement in the upper end of the tibia after the latter has been suitably prepared surgically.

It has been found that the prosthetic device described herein allows for maximum articulation that closely approximates the anatomical movement of the natural knee joint while inhibiting dislocation and providing enhanced stability. This prosthesis is intended for use in patients who have erosion of the articulating surfaces but have retention of both the collateral and cruciate ligaments of the knee and have maintained fairly good musculo-skeletal function.

The femoral component 12 should have a surface that will provide a minimum of friction and may be cast integrally of VITALLIUM or other cobalt-chromium base alloy or stainless steel, each of which can be highly polished to insure a minimum of wear, or any other rigid tissue compatible material of adequate strength. The tibial component 13 may be manufactured separately and may also be a highly polished metallic component, but is preferably formed of a suitable ceramic or high density organic polymer material, for example, ultra high molecular weight polyethylene.

While a prosthesis for a left knee has been shown and described, it is to be understood that in providing a prosthesis for the right knee, a similarly constructed femoral component, but in the mirror image of a femoral component 12, would be used, together with an identical tibial component 13.

While the foregoing description discloses a preferred embodiment of the invention, numerous modifications and alterations may be made therein without departing from the spirit and the scope of the invention as set forth in the appended claims.

What is claimed is:

1. A prosthetic knee joint comprising cooperating femoral and tibial components, said femoral component having bone fixation means for implantation in the human femur and a pair of spaced condylar support members joined by an intercondylar segment, said condylar support members comprising a medial member and a lateral member, the longitudinal axis of said medial member being disposed at an anteriorly convergent angle of from about 3 to 7 degrees with respect to the longitudinal axis of said femoral component, each of said condylar support members having a downwardly facing convex articulating surface with interior and exterior sides whose profile in transverse cross-section is defined by a circular arc extending upwardly to the interior side of said articulating surface and whose longitudinal cross-sectional configuration is defined by a condylar curve having at least three radii of curvature, each said curve comprising a central section and a pair of terminal sections, the radius of curvature of the posterior terminal section of each said curve being smaller than the radii of curvature of the central and anterior terminal sections of said curve, the condylar curve of said lateral member having at least one central portion radius of curvature larger than the central portion radii of said medial member, said tibial component having bone fixation means for implantation in the human tibia and having a pair of spaced plateau members joined by an intercondylar eminence segment, said plateau members comprising a medial and lateral bearing surface, each with interior and exterior sides, wherein the longitudinal axis of the medial and lateral bearing members is disposed at an anteriorly convergent angle of from about 3° to 7° with respect to the longitudinal axis of said tibial component, said angle of convergence of each of said bearing members being substantially equal to the angle of convergence of said medial condylar support member, each of said bearing members having an upwardly facing concave articulating surface for cooperating with the corresponding convex articulating surface of said condylar support member, defined by a circular arc whose radius of curvature is at least as large as the largest radius of curvature of said corresponding condylar support member, and said plateau bearing surfaces each having in transverse cross-section a profile defined by a portion of a circular quadrant smoothly merging to a portion that is substantially horizontally tangent to said quadrant, said quadrant portion curving upwardly to the interior side of said bearing surface to form side walls for guiding the articulating movement of the condylar support members.

2. A prosthetic knee joint according to claim 1, wherein the longitudinal axis of said lateral condylar member is substantially parallel to the longitudinal axis of said femoral component.

3. A prosthetic knee joint according to claim 1, wherein the radii of curvature for said circular quadrant portions of said plateau bearing surfaces are greater than the corresponding radii of curvature of said condylar support members in their transverse cross-section.

4. A prosthetic knee joint according to claim 1, wherein said condylar support members are anteriorly connected by a patellar articulating flange and provide circumduction in one plane.

5. A prosthetic knee joint according to claim 4, wherein said flange is non-symmetrical and has a concave bearing suface for receiving the patella.

6. A prosthetic knee joint according to claim 1, wherein said interior side walls extend in a continuous circumflex manner to form both interior and posterior guiding means.

7. A prosthetic knee joint according to claim 1, wherein said condylar support members have an inner surface on which upwardly extending fixation means are located and adapted to be received in a resected area of the femur for anchoring the femoral component in place thereon.

8. A prosthetic knee joint according to claim 1, wherein said tibial fixation means are fins extending downwardly from the under surface of each spaced plateau member and adapted to be received in a resected area of the tibia for anchoring the tibial component in place thereon.

9. A prosthetic knee joint according to claim 1, wherein said spaced condylar articulating members are constructed of metal and said tibial component is constructed of plastic material.

* * * * *